United States Patent [19]

Rametti

[11] Patent Number: 4,808,110
[45] Date of Patent: Feb. 28, 1989

[54] METHOD FOR AFFIXING AN IMPROVED DENTURE APPLIANCE

[76] Inventor: Enrico Rametti, 133 Reeger Ave., Trenton, N.J. 08610

[21] Appl. No.: 131,591

[22] Filed: Dec. 11, 1987

[51] Int. Cl.$^4$ ............................................. A61C 13/12
[52] U.S. Cl. .................................... 433/172; 433/184; 433/188
[58] Field of Search ............ 433/172, 184, 188, 168.1, 433/171

[56] References Cited

U.S. PATENT DOCUMENTS

| 1,674 | 7/1840 | Riggs | 433/184 |
| 19,858 | 4/1858 | Levett | 433/188 |
| 1,947,907 | 2/1934 | Groves | 433/188 |
| 2,867,903 | 1/1959 | Hedges | 433/184 |
| 3,745,652 | 7/1973 | Alderman | 433/184 |

FOREIGN PATENT DOCUMENTS 450709  7/1936  United Kingdom ................ 433/184

Primary Examiner—John J. Wilson
Attorney, Agent, or Firm—Sperry, Zoda & Kane

[57] ABSTRACT

A method for affixing an improved denture appliance including artificial teeth fixedly secured with respect to one another within a support member wherein the support member defines an arcuate concave mounting channel therein which is adapted to be positioned in abutment with respect to the gum tissue of a user to facilitate securement. The support member defines affixing holes formed therein with flared lower edges to allow the gum tissue of a user to grow into the holes. An initial drilling of the affixing holes will be followed by at least one month of usage of the denture appliance allowing protrusions of gum tissue to grow into the initially drilled holes. After at least one month of wearing the affixing holes will be drilled somewhat larger to allow the protrusion of gum tissue growing therein to also enlarge. Several enlargement drillings will be performed until the protrusion of the gum tissue grows to a sufficient extent to facilitate detachable firm securement of the denture appliance with respect to the gum tissue of a user.

20 Claims, 1 Drawing Sheet

METHOD FOR AFFIXING AN IMPROVED DENTURE APPLIANCE

BACKGROUND OF THE INVENTION

1. Field Of The Invention

The present invention deals with the field of devices designed for retainment of false or artificial teeth with respect to the mouth of a user. Conventional artificial teeth mounted in a plate tend to slide or move causing discomfort within the mouth of a user requiring the use of topical anesthetic and lubricants along the upper portion of the gum tissue of a user. Many designs have attempted to alleviate problems of loosening of the dentures or irritation spots normally associated with such usage.

2. Description Of The Prior Art

Many devices have been designed to overcome the difficulties of securement of artificial teeth with respect to gum tissue of a user such as shown in U.S. Pat. No. 1,674 patented July 3, 1840 to A. Riggs on Mounting Artificial Teeth; U.S. Pat. No. 19,858 patented Apr. 6, 1858 to M. Levett on a Plate For Artificial Teeth; U.S. Pat. No. 331,840 patented Dec. 8, 1885 to J. Spyer on a Dental Suction Plate Former; U.S. Pat. No. 493,800 patented Mar. 21, 1893 to J. R. Watson on a Dental Plate; U.S. Pat. No. 912,026 patented Feb. 9, 1909 to C. R. Powers on a Dental Suction Plate; U.S. Pat. No. 1,463,968 patented Aug. 7, 1923 to J. Petry on Denture; U.S. Pat. No. 1,887,970 patented Nov. 15, 1932 to L. M. Valbuena on a Dental Plate; U.S. Pat. No. 1,947,907 patented Feb. 20, 1934 to J. Groves on a Means Of Retention And Traction For Dentures; and U.S. Pat. No. 2,867,903 patented Jan. 13, 1959 to R. E. Hedges on a Means for Holding Dentures In Place.

SUMMARY OF THE INVENTION

The present invention provides an improved denture appliance including artificial teeth which are fixedly secured with respect to a support member for retainment thereof with respect to one another.

The support member defines a mounting channel normally in the lower portion thereof opposite from the location of the artificial teeth. This mounting channel is arcuate and concave to be adapted to be positioned adjacent the gum tissue of a user to facilitate detachable retainment of the support member with respect to the gum tissue.

The mounting channel defines a plurality of affixing holes therein adapted to be positioned adjacent the gum tissue of a user to allow this tissue to grow into the affixing holes to facilitate detachable placement of the support member of the improved denture appliance with respect to the gum tissue of a user.

Preferably four to ten such holes are defined in the support member. These holes are normally between $\frac{1}{8}''$ and 3/16" in diameter. The holes are normally defined in the uppermost apex of the mounting channel such that they contact the uppermost crown of the gum tissue of the user. Preferably the affixing holes are flared at the lower edges to thereby facilitate the growth of protrusions of gum tissue there into to facilitate detachable retainment of the appliance with respect to the tissue of a user.

The method of installation includes the initial formation of a plurality of the affixing holes within the concave arcuate mounting channel followed by usage of the denture appliance by placement of the mounting channel of the support member in position adjacent the gum tissue of a user for a substantial period of time normally at least one month. After this term of usage protrusions of gum tissue will tend to grow into the affixing holes in the mounting channel to further facilitate detachable retainment of the appliance with respect to the gum tissue of a user.

It is preferable that the formation of the protrusions be done in a step fashion wherein the initial drilling of the affixing hole is somewhat small to allow a small protrusion of gum tissue to grow therein. After a month or two of wearing the affixing hole will be enlarged thereby allowing further growth of the protrusion of gum tissue therein by the user utilizing the denture appliance for another month or two. This process can be repeated two to eight times to provide a sufficiently large protrusion of gum tissue to retain the appliance with respect to the gum tissue of a user and yet still allow easy removal by a user when desired.

It is an object of the present invention to provide an improved denture appliance wherein artificial teeth means are securely retained with respect to gum tissue of a user while allowing easy removal when desired.

It is an object of the present invention to provide an improved denture appliance wherein movement of artificial teeth with respect to the gum tissue of a user is virtually eliminated during usage thereof.

It is an object of the present invention to provide an improved denture appliance wherein sore spots on the gum tissue of a user due to movement of the false teeth with respect to the gum tissue of a user are eliminated.

It is an object of the present invention to provide an improved denture appliance wherein the artificial teeth are maintained in a stable position with respect to the gums of a user.

It is an object of the present invention to provide an improved denture appliance wherein holes are drilled in the mounting channel of the support member for artificial teeth thereby eliminating the usage of any additional parts or devices to retain the teeth in place with respect to the gum tissue.

It is an object of the present invention to provide an improved denture appliance wherein firmly secured dentures can be easily removed by a user without requiring any special additional tools or the like.

It is an object of the present invention to provide an improved denture appliance wherein maintenance costs are minimized.

It is an object of the present invention to provide an improved denture appliance wherein comfort is maximized.

It is an object of the present invention to provide an improved denture appliance wherein costs over and above the basic cost of the artificial teeth means is negligible.

It is an object of the present invention to provide an improved denture appliance wherein security of positioning during talking and eating is maximized.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
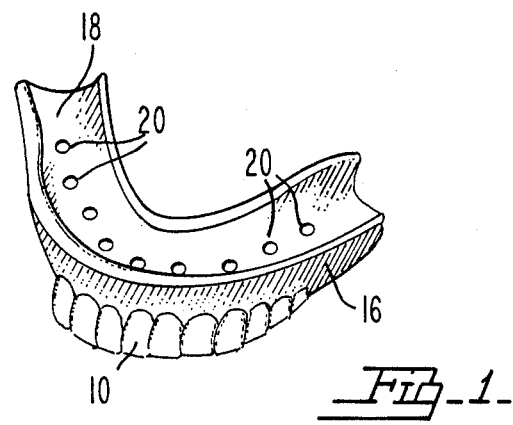
FIG. 1 is a top perspective view of an embodiment of the present invention.
Figure 2:
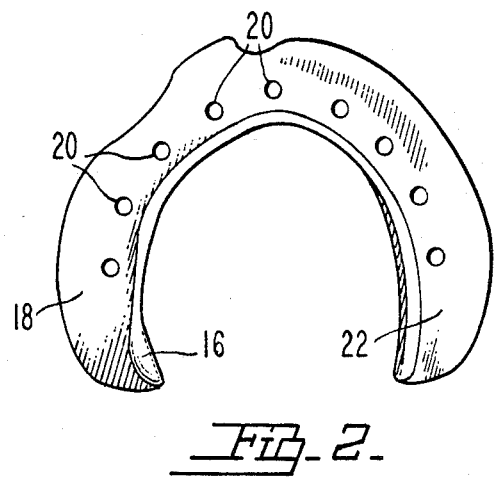
FIG. 2 is a bottom plan view of an embodiment of the present invention.

The present invention provides an artificial teeth means 10 which are adapted to be securely positioned with respect to the gum tissue 12 of a user. Artificial teeth means 10 are retained in firm securement with respect to one another by being mounted within a support member 16.

Support member 16 defines a mounting channel 18 therein which is preferably concave and arcuate to conform to the conventional shape of the gum tissue 12 of a user.

The present invention provides for the formation of a plurality of affixing hole means 20 defined in the mounting channel 18 which is preferably positioned in the undersurface 22 of support member 16. Further preferably the affixing holes 20 are positioned at the apex 24 of mounting channel 18 such that they are in abutment with the uppermost portion 44 of the gum tissue 12 of a user.

The affixing holes 20 being in abutment with respect to gum tissue 12 are adapted to allow the growth of protrusions 14 of gum tissue 12 therein in such a manner as to provide some element of retainment therebetween. To facilitate the growth of protrusions 14 it is preferable that the lower edges of affixing hole means 20 include a flaring section 26.

In the method of placement of the artificial teeth means 10 of the present invention there will be an initial drilling 28 to form an initial and somewhat small affixing hole 20. Thereafter the user will wear the improved denture appliance of the present invention for a period of at least one month during which a first protrusion 36 of gum tissue 12 will grow into the first drilled hole 28.

Figure 3:
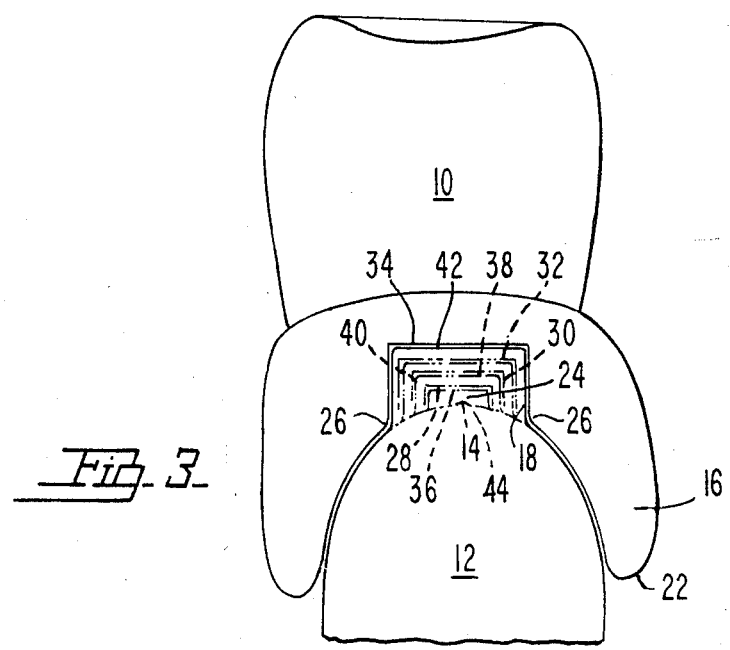
FIG. 3 is a side cross sectional view of an embodiment of the present invention.

After the first protrusion 36 of gum tissue 12 has grown basically to the maximum size allowable by the first drilled hole 28 the user will return to allow a second drilling 30 of another hole preferably concentric with respect to the first hole 28 thereby enlarging somewhat the dimensions of hole 20. Thereafter the user will again use the improved denture appliance for at least a period of one month during which the first protrusion 36 will grow to an extent as shown in FIG. 3 as a second protrusion 38. Second protrusion 38 is merely the additional growth of first protrusion 36 allowable by the enlargement of affixing holes 20 due to the second drilling 30 thereof.

This step can be repeated several times such that the enlargement of affixing hole 20 by third drilling 32 will result in the additional growth into third protrusion 40. Furthermore a fourth drilling 34 enlarging the hole 20 beyond the dimensions resulting from third drilling 32 will allow the enlargement of the protrusion to the extent of the fourth protrusion 42. Each time a new drilling is performed preferably the flaring section 26 is provided therein and the subsequent drilling is not performed until the user has had a chance to wear the denture appliance for at least a period of one month preferably two to three months. In this manner the full growth of the enlarged protrusions 36, 38, 40 and 42 is made possible. This step of enlarging and then wearing of the denture for a one to three month period can be repeated any number of times but it has been found that at least four times is required to provide sufficient detachable retainment of the support member 16 with respect to the gum tissue 12 of a user.

The number of affixing holes 20 defined within the mounting channel 18 can be any desired number from two to ten. Larger dentures would require a greater number of holes to facilitate retainment against lateral and other movement.

Preferably the size of the final resulting holes 20 will be in the order of ⅛" to 3/16" in diameter.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. A method for affixing an improved denture appliance with respect to the gum tissue of a user comprising:
   (a) constructing a support member for securing artificial teeth means with respect to one another thereon;
   (b) forming a concave arcuate mounting channel in the support member to facilitate mounting thereof with respect to the gum tissue of a user;
   (c) making a plurality of affixing hole means within the concave arcuate mounting channel;
   (d) placing the mounting channel of the support member in position adjacent the gum tissue of a user with the affixing hole means in abutment therewith for a period of time to allow a protrusion of gum tissue to grow extending into the affixing hole means to facilitate detachable secure retainment of the improved denture appliance with respect to the gum tissue of a user;
   (e) removing the support member from the mount of a user;
   (f) enlarging the affixing hole means after removal; and
   (g) replacing the mounting channel of the support member in position adjacent the gum tissue to allow growth of the protrusion of gum tissue extending into the enlarged affixing hole means.

2. A method for affixing an improved denture appliance with respect to the gum tissue of a user as defined in claim 1 wherein the concave arcuate mounting channel is formed in the undersurface of the support member to facilitate detachable secure placement thereof with respect to the gum tissue of a user.

3. A method for affixing an improved denture appliance with respect to the gum tissue of a user as defined in claim 1 further comprising:
   (a) second removing of the support member from the mouth of a user;
   (b) second enlarging of the affixing hole means after removal; and
   (c) second replacing of the mounting channel of the support member in position adjacent the gum tissue to allow further growth of the protrusion of gum tissue extending into the further enlarged affixing hole means.

4. A method for affixing an improved denture appliance with respect to the gum tissue of a user as defined in claim 3 further comprising:
   (a) third removing of the support member from the mouth of a user;
   (b) third enlarging of the affixing hole means after removal; and
   (c) third replacing of the mounting channel of the support member in position adjacent the gum tissue to allow still further growth of the protrusion of gum tissue extending into the still further enlarged affixing hole means.

5. A method for affixing an improved denture appliance with respect to the gum tissue of a user as defined in claim 4 further comprising:
   (a) fourth removing of the support member from the mouth of a user;
   (b) fourth enlarging of the affixing hole means after removal; and
   (c) fourth replacing of the mounting channel of the support member in position adjacent the gum tissue to allow even still further growth of the protrusion of gum tissue extending into the even still further enlarged affixing hole means.

6. A method for affixing an improved denture appliance with respect to the gum tissue of a user as defined in claim 1 wherein said removing, said enlarging followed by said replacing are performed four to six times to facilitate enlarging of the gum tissue protrusions.

7. A method for affixing an improved denture appliance with respect to the gum tissue of a user as defined in claim 1 further comprising flaring of the lowermost edges of the affixing hole means to facilitate growth of protrusion of gum tissue therein.

8. A method for affixing an improved denture appliance with respect to the gum tissue of a user as defined in claim 1 wherein said making of affixing hole means includes at least four individual hole members.

9. A method for affixing an improved denture appliance with respect to the gum tissue of a user as defined in claim 1 wherein said placing of the mounting channel for a period of time lasts for at least one month.

10. A method for affixing an improved denture appliance with respect to the gum tissue of a user as defined in claim 1 wherein said making of the affixing hole means include individual holes of from ⅛ to 3/16 of an inch in diameter.

11. A method for affixing an improved denture appliance with respect to the gum tissue of a user as defined in claim 1 wherein said making of a plurality of affixing hole means comprises drilling thereof.

12. A method for affixing an improved denture appliance with respect to the gum tissue of a user comprising:
   (a) constructing a support member for securing artificial teeth means with respect to one another therein;
   (b) forming a concave arcuate mounting channel in the undersurface of the support member to facilitate mounting thereof with respect to the gum tissue of a user;
   (c) drilling at least four affixing hole means within the concave arcuate mounting channel;
   (d) placing the mounting channel of the support member in position adjacent the gum tissue of a user with the affixing hole means in abutment therewith for a period of time to allow a protrusion of gum tissue to grow extending into the affixing hole means to facilitate detachable secure retainment of the improved denture appliance with respect to the gum tissue of a user;
   (e) removing the support member from the mouth of a user;
   (f) enlarging the affixing hole means after removal;
   (g) replacing the mounting channel of the support member in position adjacent the gum tissue for at least one month to allow growth of the protrusion of gum tissue extending into the enlarged affixing hole means; and
   (h) repeating of said removing and said enlarging followed by said replacing are performed three to six times to facilitate enlarging of the gum tissue protrusions to enhance retainment of the improved denture appliance upon the gum tissue of the user.

13. A method for affixing an improved denture appliance with respect to the gum tissue of a user as defined in claim 12 further comprising flaring of the lowermost edges of the affixing hole means to facilitate growth of protrusions of gum tissue therein.

14. For use with a denture appliance including artificial teeth means and a support member securing the teeth with respect to one another with the support member defining a mounting channel therein adapted to be positioned adjacent the gum tissue of a user, wherein the improvement comprises a method for affixing the denture appliance with respect to the gum tissue of a user comprising:
   (a) making a plurality of affixing hole means within the concave arcuate mounting channel;
   (b) placing the mounting channel of the support member in position adjacent the gum tissue of a user with the affixing hole means in abutment therewith for a period of time to allow a protrusion of gum tissue to grow extending into the affixing hole means to facilitate detachable secure retainment of the improved denture appliance with respect to the gum tissue of a user;
   (c) removing the support member from the mouth of a user;
   (d) enlarging the affixing hole means after removal; and
   (e) replacing the mounting channel of the support member in position adjacent the gum tissue to allow growth of the protrusion of gum tissue extending into the enlarged affixing hole means.

15. An improved method for affixing a denture appliance with respect to the gum tissue of a user as defined in claim 14 wherein said removing, said enlarging followed by said replacing are performed two to six times to facilitate enlarging of the gum tissue protrusions for more secure detachable retainment of the denture appliance with respect to the gum tissue of a user.

16. An improved method for affixing a denture appliance with respect to the gum tissue of a user as defined in claim 14 further comprising flaring of the lowermost edges of the affixing hole means to facilitate growth of protrusions of gum tissue therein.

17. An improved method for affixing a denture appliance with respect to the gum tissue of a user as defined in claim 14 wherein said making of affixing hole means includes, at least four individual hole members.

18. An improved method for affixing a denture appliance with respect to the gum tissue of a user as defined in claim 14 wherein said placing of the mounting channel for a period of time lasts for at least one month.

19. An improved method for affixing a denture appliance with respect to the gum tissue of a user as defined in claim 14 wherein said making of the affixing hole means includes individual holes of rom ⅛ to 3/16 of an inch in diameter.

20. An improved method for affixing a denture appliance with respect to the gum tissue of a user as defined in claim 14 wherein said making of a plurality of affixing hole means comprises drilling thereof.

* * * * *